United States Patent [19]

Kuga et al.

[11] Patent Number: 5,082,776
[45] Date of Patent: Jan. 21, 1992

[54] METHOD OF PRODUCING AN ADULT T CELL LEUKEMIA VIRUS FUSED ANTIGEN POLYPEPTIDE

[75] Inventors: Tetsuro Kuga; Susumu Sekine, both of Machida; Seiga Itoh, Sagamihara, all of Japan

[73] Assignee: Kyowa Hakko Kogyo Co., Ltd., Tokyo, Japan

[21] Appl. No.: 473,033

[22] Filed: Jan. 31, 1990

Related U.S. Application Data

[62] Division of Ser. No. 896,734, Aug. 15, 1986, Pat. No. 4,939,094.

[30] Foreign Application Priority Data

Aug. 28, 1985 [JP] Japan ............................. 60-188868

[51] Int. Cl.⁵ .................... C12P 21/02; C12N 15/62; C12N 15/48
[52] U.S. Cl. ................................. 435/69.7; 435/69.3; 435/172.3; 424/88; 530/350; 530/806; 530/826
[58] Field of Search .................. 435/69.7, 172.3, 239; 530/350, 806; 424/88

[56] References Cited

U.S. PATENT DOCUMENTS

| | | | |
|---|---|---|---|
| 4,349,629 | 9/1982 | Carey et al. | 435/172.3 |
| 4,431,739 | 2/1984 | Riggs | 435/252.3 |
| 4,588,681 | 5/1986 | Sawada et al. | 435/5 |
| 4,629,783 | 12/1986 | Cosand | 530/324 |
| 4,722,840 | 2/1988 | Valenzuela et al. | 435/69.7 |
| 4,724,258 | 2/1988 | Yoshida et al. | 530/350 |
| 4,751,180 | 6/1988 | Cousens et al. | 435/69.7 |

FOREIGN PATENT DOCUMENTS

| | | |
|---|---|---|
| 0139216 | 5/1985 | European Pat. Off. |
| 0152030 | 8/1985 | European Pat. Off. |
| 0181150 | 5/1986 | European Pat. Off. |
| 0185444 | 6/1986 | European Pat. Off. |

OTHER PUBLICATIONS

Virology 136: 338–347, 1984 Hattori et al. Identification of gas and env Gene Products of Human T-Cell Leukemia Virus (HTLV).

Hatanaka et al., "The pX region of HTLV-1" Chem. Abs. 105(1986) 55379x.

Davis et al., "Immune Response to Human Influenza Virus Hemagluttin Expressed in *Escherichia coli*", Gene 21 (1983) 273–284.

Seiki et al., "Human Adult T-Cell Leukemia Virus: Complete Nucleotide Sequence of the Provirus Genome Integrated in Leukemia Cell DNA", Pro Natl. Acad. Sci., USA, 80 (1983) 3618–3622.

*Primary Examiner*—Richard A. Schwartz
*Assistant Examiner*—John D. Ulm
*Attorney, Agent, or Firm*—Fitzpatrick, Cella, Harper & Scinto

[57] ABSTRACT

The present invention provides a hybrid antigen polypeptide having both antigenicity of the ATLA encoded by gag gene and that of the ATLA encoded by env gene. The hybrid antigen can be produced in a large amount and it is applicable to serum diagnosis of patients infected with antigen polypeptides such as ATLV.

4 Claims, 4 Drawing Sheets

LIGATION

METHOD OF PRODUCING AN ADULT T CELL LEUKEMIA VIRUS FUSED ANTIGEN POLYPEPTIDE

This application is a division of application Ser. No. 896,734, filed Aug. 15, 1986, now U.S. Pat. No. 4,939,094.

BACKGROUND OF THE INVENTION

The present invention relates to a fused antigen polypeptide wherein two or more antigen polypeptides are fused (referred to as "hybrid antigen polypeptide" hereinafter) and a process for producing the hybrid antigen polypeptide by using a microorganism carrying a recombinant DNA containing a DNA coding for the hybrid antigen polypeptide. Antigen-antibody reaction is applied to various fields of medical care and medical science and the hybrid antigen polypeptide of the present invention is expected to be useful in a wide field.

So far, antigen-antibody reaction has been used in various fields, specifically in the field of medical treatment such as diagnosis, therapy and prevention of diseases. The usefulness of antigen-antibody reaction is due to its high specificity which assures correctness of diagnosis and effectiveness of therapy and prevention of diseases. On the other hand, it has been known that a disease is sometimes caused by plural antigen moieties In such case, since diagnosis, therapy and prevention of the disease using one antigen moiety lead to low correctness and effectiveness due to the high specificity of antigen-antibody reaction, a mixture of two or more antigen moieties or a crude extract of pathogen has been used hitherto Prior art is explained in detail below by the example of serum diagnosis of adult T cell leukemia (referred to as ATL hereinafter).

Adult T cell leukemia virus (referred to as ATLV hereinafter) which is a synonym of human T cell leukemia virus (HTLV-I) is considered to be the causative virus of ATL. Serum diagnosis of ATLV infection is a important clinical diagnostic technique for the diagnosis of ATL and prevention of ATLV infection through blood transfusion, etc. Serum diagnosis is carried out by examining the presence of antibodies (referred to as anti-ATLA antibody hereinafter) to ATL-associated antigens (referred to as ATLA hereinafter) using antigen-antibody reaction. ATLA is a component of an ATLV particle and plural species of ATLA are known. They are divided into two large groups, i.e. ATLA group encoded by gag gene of ATLV and that encoded by env gene of ATLV. Further, each ATLA group contains plural species of ATLA different in antigenicity [Hattori et al., Virology, 136, 338-347 (1984)]. One anti-ATLA antibody reacts specifically with only one ATLA. It is known that various anti-ATLA antibodies are present in the serum of a person infected with ATLV and the antibodies vary with the individual. In such serum diagnosis, a method using a crude extract of ATL-derived cultured cells as an antigen has been tried. However, the method has various problems, for example, the high cost of cell culture, the safety problem involved in mass production of ATLV-excreting cells, limited productivity, etc. Further, the method leads to deletion of a sugar protein of a molecular weight of 46,000 daltons in the antigen polypeptide encoded by env gene.

On the other hand, recently a method for producing ATLA polypeptide encoded by gag gene or env gene of ATLV using a microorganism has been developed [K. P. Samuel et al., Science 226, 1094–1097 (1984); Kiyokawa et al., Proc. Natl. Acad. Sci. USA 81, 6202–6206 (1984); Sekine et al., Nippon Nogeikagaku Kai (The Agricultural Chemical Society of Japan) Summary of lectures in the 1984's meeting, page 440; Itamura et al., Summary of the 57th meeting of Nippon Seikagaku Kai (The Japanese Biochemical Society) in 1984, page 1079]. The ATLA polypeptide produced by the method has an antigenicity only as the ATLA encoded by gag gene or env gene and it is difficult to conduct correct diagnosis by using the single ATLA polypeptide. Therefore, use of a mixture of two ATLA polypeptides has been recommended. However, separate production of two polypeptides and use of a mixture thereof are economically disadvantageous.

SUMMARY OF THE INVENTION

The present inventors have studied about production of useful antigen polypeptides and established a method for producing a hybrid antigen polypeptide wherein two or more antigen polypeptides are fused, whereby the problem mentioned above can be solved.

The present inventors have found that a fused polypeptide wherein an ATLA polypeptide encoded by gag gene and an ATLA polypeptide encoded by env gene are fused is produced by incorporating a DNA fragment containing qag gene and a DNA fragment containing env gene into a vector DNA by a recombinant DNA technique, introducing the DNA into a microorganism and culturing the resultant microorganism.

The fused polypeptide produced by the present invention is a hybrid antigen polypeptide having both antigenicity of the ATLA encoded by gag gene and that of the ATLA encoded by env gene. According to the present invention, said hybrid antigen polypeptide can be produced in a large amount at a low cost. The hybrid antigen polypeptide of the present invention is expected to be useful not only in the field of clinical diagnosis but also in the field of preventology as polyvalent subunit vaccine.

DESCRIPTION OF THE INVENTION

The present invention provides a hybrid antigen polypeptide wherein two or more antigen polypeptides are fused, a recombinant plasmid containing a DNA fragment coding for the polypeptide, a microorganism carrying the plasmid, and processes of producing these substances.

The hybrid antigen polypeptide of the present invention is constructed by fusing two or more antigen polypeptides. As the antigen polypeptide, ATLA is mentioned as an example, and as the ATLA, product of gag gene of ATLV, that of env gene of ATLV or a part thereof is used. The hybrid antigen polypeptide of the present invention is produced by incorporating ligated two or more gene DNAs coding for antigen polypeptides into a vector plasmid, introducing the resultant recombinant plasmid into a host microorganism and culturing the resultant transformant.

Construction of the recombinant plasmid of the present invention is carried out by the following method.

A recombinant plasmid is constructed by incorporating two or more DNAs coding for antigen peptides such as a DNA coding for the product of gag gene of ATLV and a DNA coding for the product of env gene of ATLV into a vector DNA in translational reading frame by recombinant DNA technology.

Figure 3:
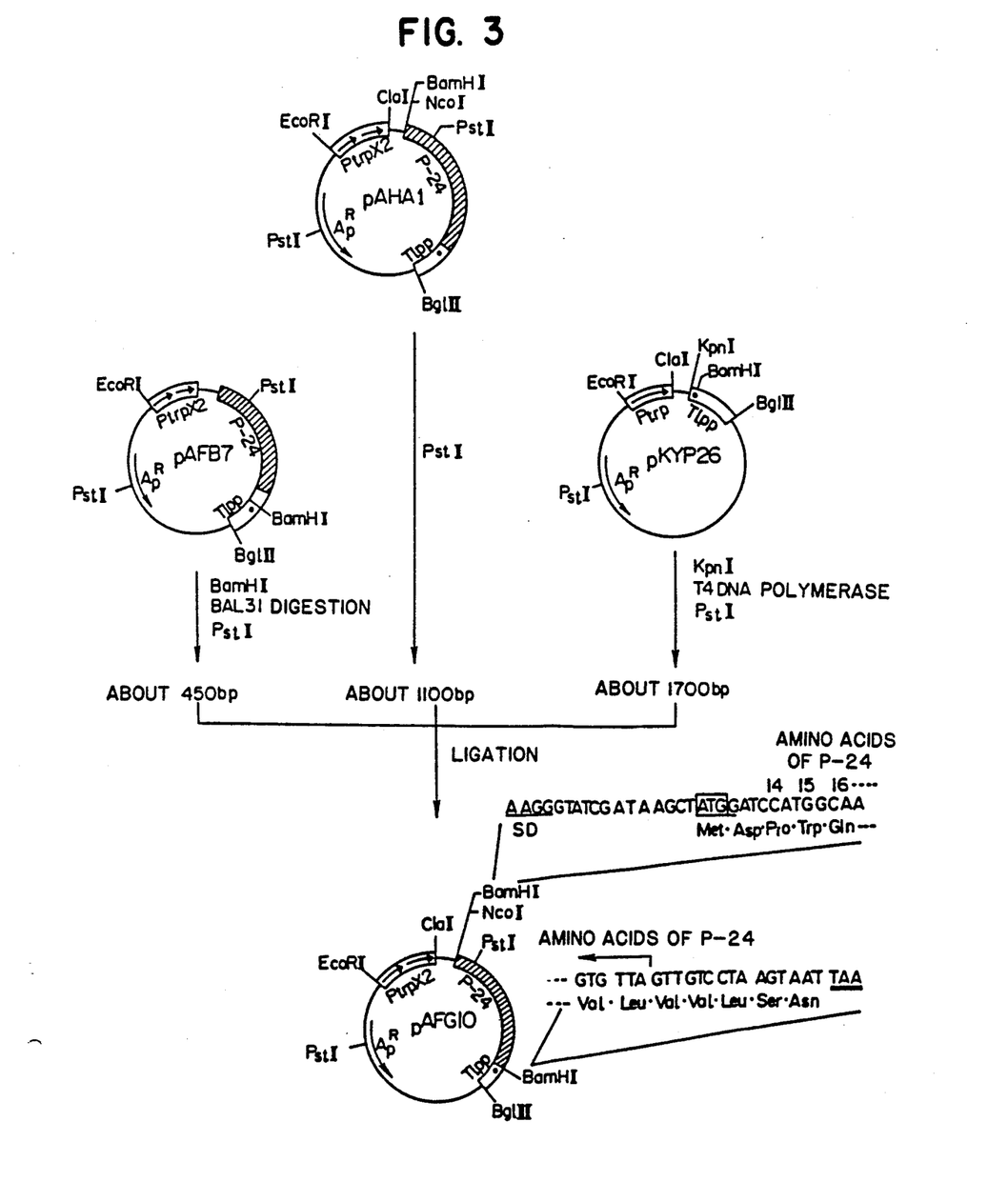
FIG. 3 shows the process for constructing plasmid pAFG10.

As the source of DNAs coding for the product of gag gene of ATLV and that of env gene of ATLV, for example, pATK03, pATK100 [Seiki, et al., Proc. Natl Acad Sci. USA, 80, 3618-3622 (1983)] and derivative plasmids thereof are used. As the DNA coding for the product of gag gene pTAG424A (FERM BP-341) and pAFA10 (ATCC 39582) are preferably used. As the DNA coding for the product of env gene, pEFM2 is preferably used. *Escherichia coli* carrying pEFM2 was deposited with the American Type Culture Collection on Aug. 8, 1985 as ATCC 53228. As shown in FIG. 3, pEFM2 has a structure which contributes to the expression of a part of the antigen polypeptide encoded by the env gene of ATLV under the control of tryptophan promoter. Amino acid sequence of the polypeptide expressed by pEFM2 and nucleotide sequence of the gene are illustrated in Table 1.

TABLE 1

→ amino acids encoded by env gene

```
         10           20           30           40           50           60
ATGGATCCATGCTGCTGTACTCTCACAATTGGAGTCTCCTCATACCACTCTAAACCCTGC
Met Asp Pro Cys Cys Cys Thr Leu Thr Ile Gly Val Ser Ser Tyr His Ser Lys Pro Cys 70           80           90          100          110          120
AATCCTGCCCAGCCAGTTTGTTCGTGGACCCTCGACCTGCTGGCCCTTTCAGCAGATCAG
Asn Pro Ala Gln Pro Val Cys Ser Trp Thr Leu Asp Leu Leu Ala Leu Ser Ala Asp Gln 130          140          150          160          170          180
GCCCTACAGCCCCCCTGCCCTAACCTAGTAAGTTACTCCAGCTACCATGCCACCTATTCC
Ala Leu Gln Pro Pro Cys Pro Asn Leu Val Ser Tyr Ser Ser Tyr His Ala Thr Tyr Ser 190          200          210          220          230          240
CTATATCTATTCCCTCATTGGACTAAGAAGCCAAACCGAAATGGCGGAGGCTATTATTCA
Leu Tyr Leu Phe Pro His Trp Thr Lys Lys Pro Asn Arg Asn Gly Gly Gly Tyr Tyr Ser 250          260          270          280          290          300
GCCTCTTATTCAGACCCTTGTTCCTTAAAGTGCCCATACCTGGGGTGCCAATCATGGACC
Ala Ser Tyr Ser Asp Pro Cys Ser Leu Lys Cys Pro Tyr Leu Gly Cys Gln Ser Trp Thr 310          320          330          340          350          360
TGCCCCTATACAGGAGCCGTCTCCAGCCCCTACTGGAAGTTTCAACACGATGTCAATTTT
Cys Pro Tyr Thr Gly Ala Val Ser Ser Pro Tyr Trp Lys Phe Gln His Asp Val Asn Phe 370          380          390          400          410          420
ACTCAAGAAGTTTCACGCCTCAATATTAATCTCCATTTTTCAAAATGCGGTTTTCCCTTC
Thr Gln Glu Val Ser Arg Leu Asn Ile Asn Leu His Phe Ser Lys Cys Gly Phe Pro Phe 430          440          450          460          470          480
TCCCTTCTAGTCGACGCTCCAGGATATGACCCCATCTGGTTCCTTAATACCGAACCCAGC
Ser Leu Leu Val Asp Ala Pro Gly Tyr Asp Pro Ile Trp Phe Leu Asn Thr Glu Pro Ser 490          500          510          520          530          540
CAACTGCCTCCCACCGCCCCTCCTCTACTCCCCCACTCTAACCTAGACCACATCCTCGAG
Gln Leu Pro Pro Thr Ala Pro Pro Leu Leu Pro His Ser Asn Leu Asp His Ile Leu Glu 550          560          570          580          590          600
CCCTCTATACCATGGAAATCAAAACTCCTGACCCTTGTCCAGTTAACCCTACAAAGCACT
Pro Ser Ile Pro Trp Lys Ser Lys Leu Leu Thr Leu Val Gln Leu Thr Leu Gln Ser Thr 610          620          630          640          650          660
AATTATACTTGCATTGTCTGTATCGATCGTGCCAGCCTCTCCACTTGGCACGTCCTATAC
Asn Tyr Thr Cys Ile Val Cys Ile Asp Arg Ala Ser Leu Ser Thr Trp His Val Leu Tyr 670          680          690          700          710          720
TCTCCCAACGTCTCTGTTCCATCCTCTTCTTCTACCCCCCTCCTTTACCCATCGTTAGCG
Ser Pro Asn Val Ser Val Pro Ser Ser Ser Thr Pro Leu Leu Tyr Pro Ser Leu Ala 730          740          750          760          770          780
CTTCCAGCCCCCCACCTGACGTTACCATTTAACTGGACCCACTGCTTTGACCCCCAGATT
Leu Pro Ala Pro His Leu Thr Leu Pro Phe Asn Trp Thr His Cys Phe Asp Pro Gln Ile 790          800          810          820          830          840
CAAGCTATAGTCTCCTCCCCCTGTCATAACTCCCTCATCCTGCCCCCCTTTTCCTTGTCA
Gln Ala Ile Val Ser Ser Pro Cys His Asn Ser Leu Ile Leu Pro Pro Phe Ser Leu Ser
```

TABLE 1-continued

```
    amino acids encoded by env gene  ←─────────────────┐
   850         860         870         880            │
CCTGTTCCCACCCTAGGATCCCGCTCCCGCCGAGCGGTACCTAAG
Pro Val Pro Thr Leu Gly Ser Arg Ser Arg Arg Ala Val Pro Lys
```

The polypeptide has the structure wherein Met-Asp-Pro-Cys and Lys are respectively attached to the N-terminal and the C-terminal of the peptide from the 6th amino acid cysteine to the 295th amino acid proline of the gp62 in the antigen polypeptides encoded by the env gene of ATLV, amino acid sequence being numbered excluding the signal peptide 20 amino acids at the N-terminal.

The antigen polypeptide encoded by the env gene is known to be a coat protein antigen (surface antigen) expressible by ATLV infection and is expected to be used for the purpose of diagnosis of ATLV infection, prevention of ATLV infection and therapy of ATL and as subunit vaccine.

As the vector DNA, any vector DNA can be utilized, provided that the inserted DNA is expressible in a microorganism. It is preferred to use a plasmid which includes a suitable promoter such as a tryptophan (trp) or lactose (lac) promoter downstream from which the subject DNA can be inserted. The downstream insertion site must be adjusted to have a suitable distance such as 6–18 base pairs, between the Shine-Dalgarno sequence (hereinafter referred to as SD sequence) and the translation initiation codon (ATG). One of the most suitable plasmids is pGEL1.

Escherichia coli carrying pGEL1 was deposited with the Fermentation Research Institute, Agency of Industrial Science and Technology (FRI) on Oct. 6, 1984 as Escherichia coli IGEL1, FERM BP-629.

Further, a plasmid having a transcriptional termination signal derived from Escherichia coli, for example pKYP26, is preferably used. Escherichia coli carrying pKYP26 was deposited with FRI on Aug. 8, 1985 as Escherichia coli IKYP26, FERM BP-863. The plasmid has the structure illustrated in FIG. 2 and contains the transcriptional termination signal of Escherichia coli lipoprotein (referred to as "lpp" hereinafter) between the cleavage sites for restriction enzymes BamHI and BglII. The DNA sequence of GGTACCTAAG-TAATTAAGGATCC is introduced upstream from the signal using a synthetic DNA. When a DNA fragment coding for a polypeptide is inserted upstream from the DNA sequence, protein synthesis terminates at one of the protein synthesis terminal codons (the TAA sequences illustrated by underline in the above base sequence) derived from the synthetic DNA Recombination of a DNA coding for the antigen polypeptide and a vector DNA is generally carried out using recombinant DNA methods in which restriction enzymes are used to digest both DNAs followed by ligation using T4DNA ligase Ligation may be conducted by a method employing fill-in reaction with DNA polymerase I.Klenow fragment, fill-in reaction or cut-off reaction with T4DNA polymerase or a method using DNA linker.

The reaction conditions necessary for the above-described preparation of the recombinant plasmid are generally as follows. DNA digestion with restriction enzymes is normally carried out by 15 minutes–24 hours digestion of 0.1–100 μg of DNA, at 18°–42° C., preferably 32°–38° C., using 0.1–300 units, preferably 1–3 units, of restriction enzyme per 1 μg of DNA in 2–200 mM, preferably 10–40 mM Tris-HCl (pH 6 0–9.5, preferably pH 7.0–8.0), 1–200 mM NaCl and 2–20 mM, preferably 5–10 mM MgCl$_2$. The reaction is terminated by heating at 55°–75° C., preferably 63°–70° C., for 5–30 minutes. The restriction enzymes may be inactivated by reagents such as phenol and diethyl pyrocarbonate.

Purification of the DNA fragments formed by the cleavage with restriction enzymes is carried out by low gelling temperature agarose gel electrophoresis [L. Wieslander: Analytical Biochemistry 98, 305 (1979), referred to as LGT method hereinafter] or polyacrylamide gel electrophoresis [A. M. Maxam et al.: Proc. Natl. Acad. Sci., 74, 560 (1977)]. Ligation of DNA fragments is conducted at 1°–37° C., preferably 3°–20° C., for 15 minutes to 72 hours, preferably 2–20 hours using 0.1–10 units of T4DNA ligase in 2–200 mM, preferably 10–70 mM Tris-HCl (pH 6.0–9.5, preferably pH 7.0–8.0), 2–20 mM, preferably 5–10 mM MgCl$_2$, 0.1–10 mM, preferably 0.5–2 mM ATP and 1–50 mM, preferably 5–10 mM dithiothreitol.

The recombinant DNA formed by the ligation reaction is introduced into Escherichia coli by the method of S. N. Cohen et al: Proc Natl Acad. Sci., USA 69, 2110 (1972).

Isolation of the plasmid DNA from Escherichia coli carrying the DNA is carried out in accordance with the method of H. C. Birnboim, et al.: Nucleic Acids Research 7, 1513 (1979).

Plasmid DNA is digested with 1–10 kinds of restriction endonucleases and the cleavage sites are examined by agarose gel electrophoresis or polyacrylamide gel electrophoresis. Further, if necessary, the base sequence of the DNA is determined by the method of Maxam-Gilbert [Proc. Natl. Acad. Sci. USA, 74, 560 (1977)] or the method of Sanger [Sanger, et al.: Proc. Natl. Acad. Sci. USA, 74, 5463 (1977); Amersham Co., M13 cloning and sequencing handbook] using M13 phage.

Recombinant plasmid DNAs are produced under the foregoing conditions.

The hybrid antigen polypeptide of the present invention is produced by the following method.

That is, Escherichia coli K-12 HB101 [Bolivar et al., Gene 2, 75 (1977)] is transformed with a plasmid (e.g. pETI7) and an Escherichia coli strain carrying pETI7 is selected from the ampicillin resistant (referred to as Ap$^R$ hereinafter) colonies. The Escherichia coli strain carrying pETI7 is cultured in a medium to produce the hybrid antigen polypeptide in the culture broth.

As the medium to be used herein, either a synthetic medium or a natural medium can be used so long as it is suitable for the growth of Escherichia coli and the production of the hybrid antigen polypeptide.

As the carbon source, glucose, fructose, lactose, glycerol, mannitol, sorbitol, etc. may be used. As the nitrogen source, NH$_4$Cl, (NH$_4$)$_2$SO$_4$, casamino acid, yeast extract, polypeptone, meat extract, Bacto-Tryptone, corn steep liquor, etc may be used. In addition, nutrients such as K$_2$HPO$_4$, KH$_2$PO$_4$, NaCl, MgSO$_4$, vitamine B$_1$ and MgCl$_2$ may be used.

Culturing is carried out at pH 5.5–8.5 and at 18°–40° C. with aeration and stirring.

After culturing for 5–90 hours, the hybrid antigen polypeptide is accumulated in cultured cells. The collected cells are treated with lysozyme, disrupted by repeated freezing and thawing and subjected to centrifugation. The thus obtained supernatant fluid is subjected to extraction according to a conventional method for extraction of polypeptides to recover the polypeptide.

Detection of the polypeptide is carried out by heat-dissolving the cultured cells directly in Sample buffer of Laemmli [Laemmli, Nature, 227, 680 (1970)] and subjecting the solution to SDS-polyacrylamide gel electrophoresis (the method of Laemmli: the reference mentioned above), followed by Coomassie Brilliant Blue staining [ed. by Ozeki & Shimura, Bunshi Idengaku Jikkenho (Experimental Method for Molecular Genetics), published by Kyoritsu Shuppan p 353, 1983].

Certain specific embodiments of the invention are illustrated by the following representative examples.

EXAMPLE 1

Isolation and Purification of Plasmid pKYP26 and pEFM2:

*Escherichia coli* IKYP26 (FERM BP-863) carrying pKYP26 and *Escherichia coli* EEFM2 (ATCC 53228) carrying pEFM2 were cultured in 10 ml of L medium (1% Bacto-Tryptone, 0.5% yeast extract, 1% NaCl, pH 7.5) containing 50 µg/ml ampicillin at 37° C. for 18 hours. The whole culture broth was inoculated into 1 l of L medium containing 50 µg/ml ampicillin and cultured at 37° C. After 4 hours, 170 µg/ml chloramphenicol was added and culturing was continued at 37° C. for 16 hours. Cells were collected by centrifugation (5,000 rpm, 10 minutes) and washed with 0.8% NaCl. The washed cells were suspended in 20 ml of 50 mM Tris-HCl (pH 8.0) and cooled with ice. 8 ml of 10 mg/ml lysozyme was added and the mixture was allowed to stand under ice cooling for 10 minutes. 9.6 ml of 0.5M EDTA was added and the mixture was allowed to stand under ice cooling for 10 minutes. 2.3 ml of 2% Triton X-100 (product of Wako Junyaku Kogyo Co., Ltd.) was added and the mixture was allowed to stand under ice cooling for one hour. The mixture was subjected to ultracentrifugation at 50,000×g at 4° C. for one hour to obtain about 40 ml of a supernatant. The pH of the supernatant was adjusted to 12.5 with 3M NaOH and the supernatant was stirred gently at room temperature for 10 minutes. After the pH was readjusted to 8 5 with 2M Tris-HCl (pH 7.5), the mixture was stirred for 3 minutes. The volume of the solution was about 55 ml at this point. 5M NaCl (1/9 volume of the solution) and phenol saturated with 10 mM Tris-HCl (pH 7.5) and 1 mM EDTA (equal to volume of the solution) were added. The mixture was vigorously stirred and subjected to low pressure centrifugation (3,300 rpm, 10 minutes, the same conditions will be employed hereinafter) to recover a water layer (this treatment is referred to as "phenol extraction" hereinafter). 5 mg/ml RNase A (product of Sigma) (1/250 volume of the water layer) was added and RNA decomposition reaction was carried out at 37° C. for one hour. Then, 5M NaCl (1/5 volume of the reaction mixture) and 30% PEG 6000 (product of Nakarai Kagaku Yakuhin Co.) (⅔ volume of the reaction mixture) were added. The mixture was allowed to stand at −20° C. for 2 hours. A precipitate recovered by centrifugation was dissolved in 2 ml of a solution comprising 10 mM Tris-HCl (pH 7.5) and 1 mM EDTA. 0.5% sodium dodecyl sulfate was added and 50 µg/ml Proteinase K (product of Sigma) was added. Protein decomposition reaction was carried out at 37° C. for one hour. Phenol extraction was repeated three times and equal amount of chloroform was added. The mixture was vigorously stirred and subjected to low pressure centrifugation to recover a water layer. 3M sodium acetate (1/10 volume of the water layer) and ethanol (2.5 times volume of the water layer) were added. The mixture was allowed to stand at −20° C. for one hour. A precipitate was recovered by centrifugation with cooling (4° C., 11,000 rpm, 10 minutes) and dissolved in 1 ml of a solution comprising 10 mM Tris-HCl (pH 7.5) and 1 mM EDTA. Thus, 800 µg each of pKYP26 and pEFM2 were obtained. The structure of pKYP26 was confirmed by cleavage with EcoRI, KpnI, BamHI, BglII and PstI and agarose gel electrophoresis. The structure of pEFM2 was confirmed by cleavage with XhoI, KpnI, BglII, HpaI and PstI and agarose gel electrophoresis.

EXAMPLE 2

Construction of a plasmid containing p24 Gene of ATLV:

(1) Construction of pAFB7

5 µg of pGEL1 obtained from *Escherichia coli* IGEL1 (FERM BP-629) by a conventional method was dissolved in 40 µl of a solution comprising 10 mM Tris-HCl (pH 7.5), 7 mM MgCl₂, 6 mM mercaptoethanol and 100 mM NaCl (referred to as Y-100 buffer solution hereinafter). 10 units of restriction enzyme PstI (product of Takara Shuzo Co., the restriction enzymes used hereinafter are all products of Takara Shuzo Co., unless otherwise specified) and 8 units of BamHI were added and digestion reaction was carried out at 37° C. for 2 hours. About 0.2 µg of a DNA fragment of about 1,700 bp containing lpp terminator was recovered from the reaction solution by the LGT method.

Separately, 10 µg of pGEL1 was dissolved in 100 µl of Y-100 buffer solution and 16 units of restriction enzyme PstI was added. Digestion reaction was carried out at 37° C. for one hour. After confirmation of the digestion with PstI by agarose gel electrophoresis, 3 units of restriction enzyme HpaI was added and partial digestion reaction with HpaI was carried out at 37° C. for 30 minutes. About 0.2 µg of a partially digested DNA fragment of about 940 bp containing trp promoter was obtained from the reaction solution by the LGT method.

Figure 1:
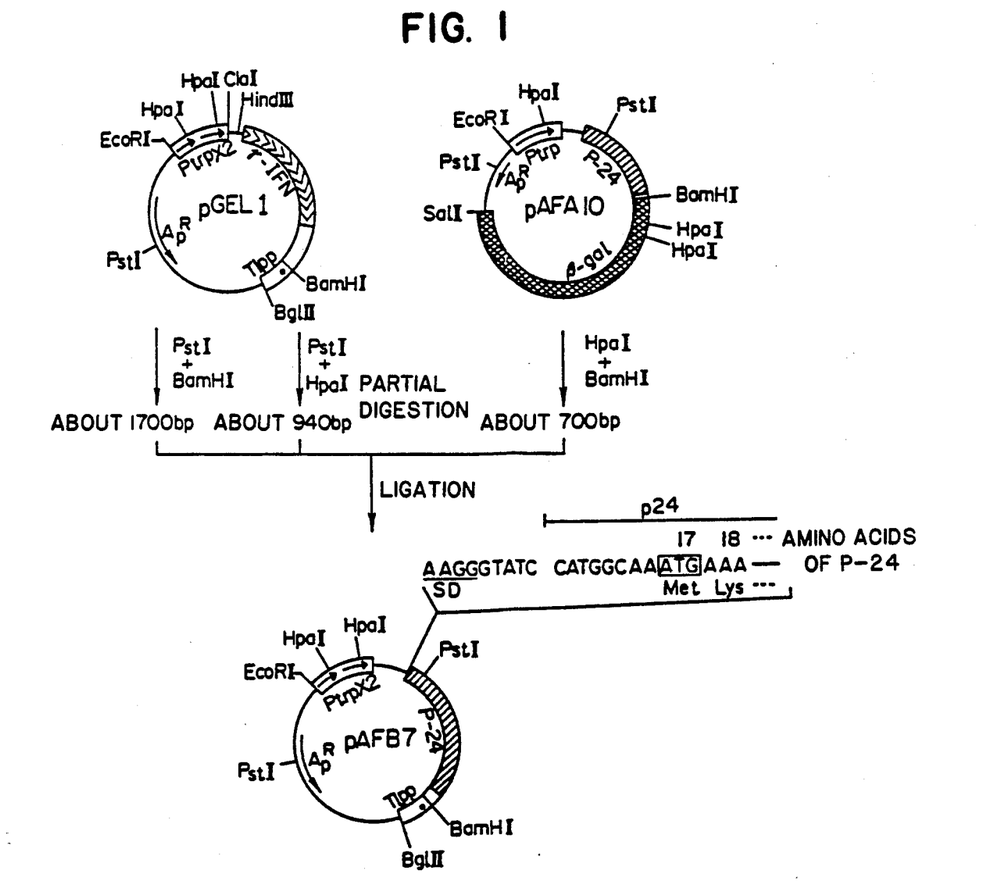
FIG. 1 shows the process for constructing plasmid pAFB7.

Then, 30 µg of pAFA10 which is the plasmid carried on ATCC 39582 strain and illustrated in FIG. 1 was dissolved in 250 µl of Y-100 buffer solution. 140 units of restriction enzyme HpaI and 30 units of BamHI were added and digestion reaction was carried out at 37° C. for 3 hours. About 0.5 µg of a DNA fragment of about 700 bp containing p24 gene was obtained from the reaction solution by the LGT method.

About 0.1 µg of PstI-BamHI fragment (about 1,700 bp) derived from pGEL1, about 0.15 µg of PstI-HpaI fragment (about 940 bp) derived from pGEL1, about 0.2 µg of HpaI-BamHI fragment (about 700 bp) derived from pAFA10 were dissolved in 20 µl of a solution comprising 20 mM Tris-HCl (pH 7.5), 10 mM MgCl₂, 10 mM dithiothreitol and 1 mM ATP (referred to as T4DNA ligase buffer hereinafter). 3 units of T4DNA ligase (product of Takara Shuzo Co.) was added and ligation reaction was carried out at 4° C. for 16 hours.

*Escherichia coli* HB101 [Bolivar et al., Gene 2, 75 (1977)] was transformed using the reaction solution to obtain Ap$^R$ colonies Plasmid DNA, pAFB7 illustrated in FIG. 1 was obtained from one of the colonies by the method of Birnboim et al. [Nucleic Acids Research 7, 1513 (1979)].

(2) Construction of pAAB6

Figure 2:
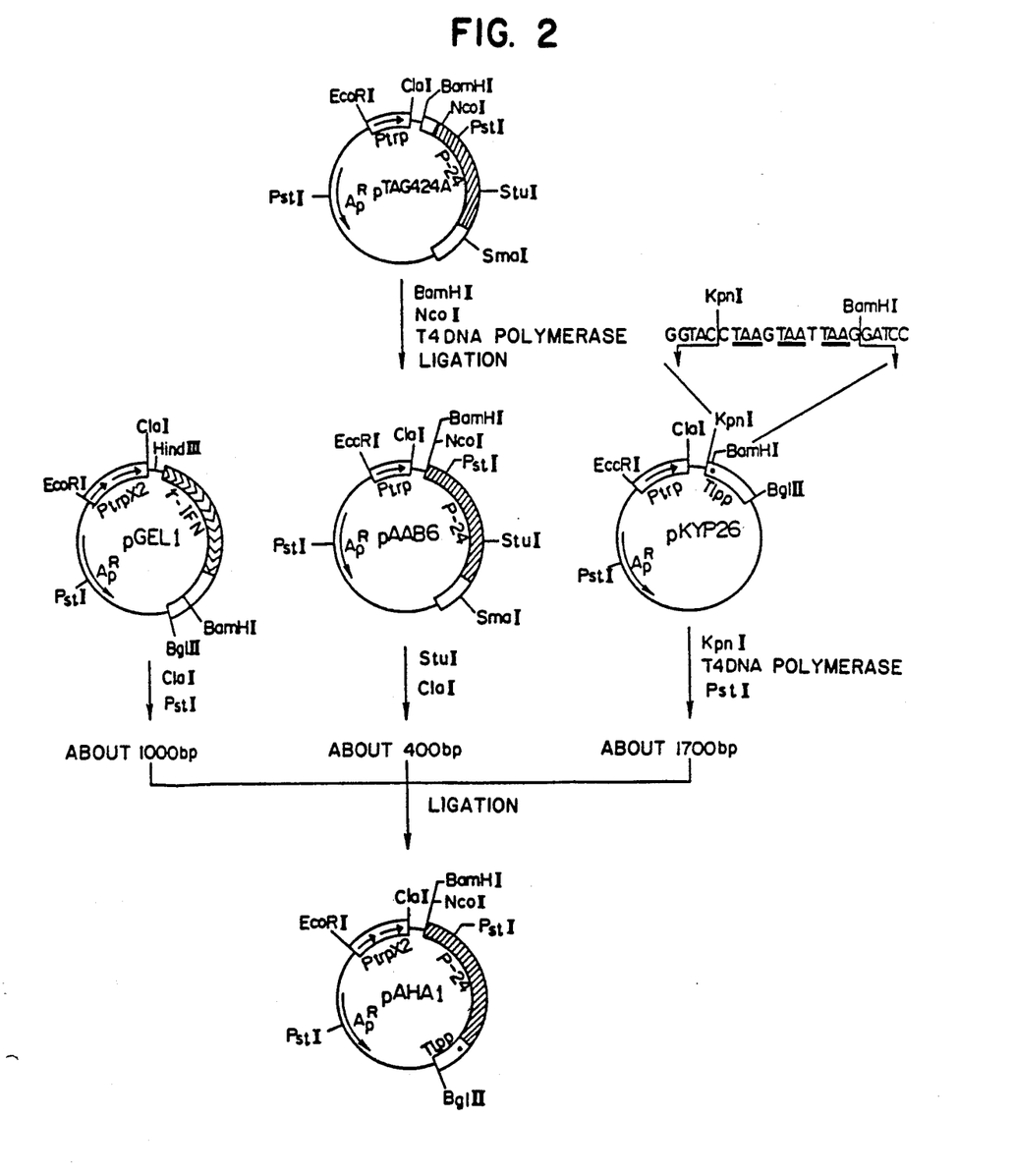
FIG. 2 shows the process for constructing plasmid pAHA1.

2 μg of pTAG424A which is a plasmid carried on FERM BP-341 strain and illustrated in FIG. 2 (Japanese Published Unexamined Patent Application No. 61534/85) was dissolved in 20 μl of Y-100 buffer solution 4 units of restriction enzyme BamHI was added and digestion reaction was carried out at 37° C. for 2 hours. Then, the NaCl concentration in the solution was adjusted to 150 mM and 4 units of restriction enzyme NcoI (product of Nippon Gene Co.) was added. Digestion reaction was carried out at 37° C. for 2 hours. The BamHI-NcoI cleaved DNA was dissolved in 20 μl of a solution comprising 33 mM Tris-acetic acid (pH 7.9), 66 mM potassium acetate, 10 mM magnesium acetate, 5 mM dithiothreitol and 0.4 mM each dATP, dCTP, dGTP and dTTP (referred to as T4DNA polymerase buffer hereinafter). One unit of T4DNA polymerase (product of Takara Shuzo Co.) was added and reaction was carried out at 37° C. for 30 minutes.

The resulting solution was mixed with 20 μl of T4DNA ligase buffer and 3 units of T4DNA ligase was added. Ligation reaction was carried out at 4° C. for 18 hours.

*Escherichia coli* HB101 was transformed using the reaction solution to obtain Ap$^R$ colonies Plasmid DNA, pAAB6 illustrated in FIG. 2 was recovered from one of the colonies by the method of Birnboim et al.

(3) Construction of pAHA1

15 μg of pAAB6 obtained above was dissolved in 100 μl of Y-100 buffer solution and 15 units of restriction enzyme StuI and 20 units of ClaI (product of New England Bio Labs) were added. Digestion reaction was carried out at 37° C. for 3 hours. About 0.3 μg of a DNA fragment of about 400 bp containing the first half of p24 gene was obtained from the reaction solution by the LGT method.

Then, 5 μg of pGEL1 was dissolved in 40 μl of Y-100 buffer solution and 5 units of restriction enzyme ClaI (product of New England Bio Labs) and 8 units of PstI were added. Digestion reaction was carried out at 37° C. for 2 hours. About 0.2 μg of a DNA fragment of about 1,000 bp containing trp promoter was obtained from the reaction solution by the LGT method.

Separately, 2 μg of pKYP26 obtained in Example 1 was dissolved in 30 μl of a solution comprising 10 mM Tris-HCl (pH 7.5), 7 mM MgCl$_2$, 6 mM mercaptoethanol and 10 mM NaCl (referred to as Y-10 buffer solution hereinafter). 5 units of restriction enzyme KpnI was added and digestion reaction was carried out at 37° C. for 2 hours. The KpnI cleaved DNA was dissolved in 20 μl of T4DNA polymerase buffer and one unit of T4DNA polymerase was added. Reaction was carried out at 37° C. for 30 minutes. The DNA reaction solution was dissolved in 30 μl of Y-100 buffer solution and 4 units of restriction enzyme PstI was added. Digestion reaction was carried out at 37° C. for 2 hours. About 0.2 μg of a DNA fragment of about 1,700 bp containing lpp terminator was obtained from the reaction solution by the LGT method.

About 0.1 μg of the StuI-ClaI fragment (about 400 bp) derived from pAAB6, about 0.2 μg of the ClaI-PstI fragment (about 1,000 bp) derived from pGEL1 and about 0.1 μg of the KpnI-PstI fragment (about 1,700 bp) derived from pKYP26 were dissolved in 30 μl of T4DNA ligase buffer. 4 units of T4DNA ligase was added and ligation reaction was carried out at 4° C. for 18 hours.

*Escherichia coli* HB101 was transformed using the reaction solution to obtain Ap$^R$ colonies. Plasmid DNA, pAHA1 illustrated in FIG. 2 was recovered from one of the colonies by the method of Birnboim et al.

(4) Construction of pAFG10

5 μg of pAHA1 obtained above was dissolved in 50 μl of Y-100 buffer solution and 8 units of restriction enzyme PstI was added Digestion reaction was carried out at 37° C. for 2 hours. About 0.5 μg of a DNA fragment of about 1,100 bp containing trp promoter and an N-terminal part of p24 gene was obtained from the reaction solution by the LGT method.

Then, 6 μg of pAFB7 constructed in step (1) was dissolved in 30 μl of Y-100 buffer solution. 8 units of restriction enzyme BamHI was added and digestion reaction was carried out at 37° C. for 2 hours. 5 μl of a solution comprising 0 2M Tris-HCl (pH 8.0), 120 mM CaCl$_2$, 120 mM MgCl$_2$, 2M NaCl and 10 mM EDTA was added to the reaction solution. 15 μl of sterilized water was added and the solution was kept at 30° C. for 3 minutes. 10 units of BAL31 nuclease (product of Bethesda Research Laboratories) was added and decomposition reaction was carried out at 30° C. for 80 seconds. After reaction, phenol extraction was carried out and a DNA was recovered by ethanol precipitation. The DNA was dissolved in 30 μl of Y-100 buffer solution and 8 units of restriction enzyme PstI was added. Digestion reaction was carried out at 37° C. for 2 hours. About 0.1 μg of a DNA fragment of about 450 bp containing p24 gene was obtained from the reaction solution by the LGT method.

About 0.2 μg of the PstI fragment (about 1,100 bp) derived from pAHA1, 0.1 μg of the PstI-BAL31 nuclease decomposition fragment (about 450 bp) derived from pAFB7 and 0.1 μg of the KpnI-PstI fragment (about 1,700 bp) derived from pKYP26 were dissolved in 30 μl of T4DNA ligase buffer. 6 units of T4DNA ligase was added and ligation reaction was carried out at 4° C. for 18 hours.

*Escherichia coli* HB101 was transformed using the reaction solution to obtain Ap$^R$ colonies. Plasmid DNA, pAFG10 illustrated in FIG. 3 was recovered from one of the colonies by the method of Birnboim et al. The base sequence of the C-terminal region coding for p24 was determined and it was confirmed that the region contained the C-terminal of p24 and Val·Val·Leu·Ser·Asn was attached thereto. The amino acid sequence of the polypeptide encoded by pAFG10 and the base sequence of the gene are illustrated in Table 2.

TABLE 2 amino acids encoded by p24 gene →

```
         10         20         30         40         50         60
ATGGATCCATGGCAAATGAAAGACCTACAGGCCATTAAGCAAGAAGTCTCCCAAGCAGCC
Met Asp Pro Trp Gln Met Lys Asp Leu Gln Ala Ile Lys Gln Glu Val Ser Gln Ala Ala 70         80         90        100        110        120
CCTGGGAGCCCCCAGTTTATGCAGACCATCCGGCTTGCGGTGCAGCAGTTTGACCCCACT
Pro Gly Ser Pro Gln Phe Met Gln Thr Ile Arg Leu Ala Val Gln Gln Phe Asp Pro Thr 130        140        150        160        170        180
GCCAAAGACCTCCAAGACCTCCTGCAGTACCTTTGCTCCTCCCTCGTGGCTTCCCTCCAT
Ala Lys Asp Leu Gln Asp Leu Leu Gln Tyr Leu Cys Ser Ser Leu Val Ala Ser Leu His 190        200        210        220        230        240
CACCAGCAGCTAGATAGCCTTATATCAGAGGCCGAAACCCGAGGTATTACAGGTTATAAC
His Gln Gln Leu Asp Ser Leu Ile Ser Glu Ala Glu Thr Arg Gly Ile Thr Gly Tyr Asn 250        260        270        280        290        300
CCATTAGCCGGTCCCCTCCGTGTCCAAGCCAACAATCCACAACAACAAGGATTAAGGCGA
Pro Leu Ala Gly Pro Leu Arg Val Gln Ala Asn Asn Pro Gln Pro Gln Gly Leu Arg Arg 310        320        330        340        350        360
GAATACCAGCAACTCTGGCTCGCCGCCTTCGCCGCCCTGCCGGGGAGTGCCAAAGACCCT
Glu Tyr Gln Gln Leu Trp Leu Ala Ala Phe Ala Ala Leu Pro Gly Ser Ala Lys Asp Pro 370        380        390        400        410        420
TCCTGGGCCTCTATCCTCCAAGGCCTGGAGGAGCCTTACCACGCCTTCGTAGAACGCCTC
Ser Trp Ala Ser Ile Leu Gln Gly Leu Glu Glu Pro Tyr His Ala Phe Val Glu Arg Leu 430        440        450        460        470        480
AACATAGCTCTTGACAATGGGCTGCCAGAAGGCACGCCCAAAGACCCCATCTTACGTTCC
Asn Ile Ala Leu Asp Asn Gly Leu Pro Glu Gly Thr Pro Lys Asp Pro Ile Leu Arg Ser 490        500        510        520        530        540
TTAGCCTACTCCAATGCAAACAAAGAATGCCAAAAATTACTACAGGCCCGAGGACACACT
Leu Ala Tyr Ser Asn Ala Asn Lys Glu Cys Gln Lys Leu Leu Gln Ala Arg Gly His Thr 550        560        570        580        590        600
AATAGCCCTCTAGGAGATATGTTGCGGGCTTGTCAGACCTGGACCCCCAAAGACAAAACC
Asn Ser Pro Leu Gly Asp Met Leu Arg Ala Cys Gln Thr Trp Thr Pro Lys Asp Lys Thr
``` amino acids
encoded by p24 gene
←

```
      610        620
AAAGTGTTAGTTGTCCTAAGTAAT
Lys Val Leu Val Val Leu Ser Asn
```

EXAMPLE 3

Construction of Recombinant Plasmid pETI7 Coding for a Hybrid Antigen Polypeptide Wherein an Antigen Polypeptide Encoded by gag Gene of ATLV and an Antigen Polypeptide Encoded by env Gene of ATLV are Fused 10 μg of recombinant plasmid pAFG10 obtained in Example 2 was dissolved in 100 μl of Y-100 buffer solution. 10 units of restriction enzyme XhoI and 2 units of StuI were added and digestion reaction was carried out at 37° C. for 3 hours.

About 0.5 μg of a DNA fragment of about 630 bp containing trp promoter and the first half of p24 gene was obtained from the reaction solution by the LGT method.

Then, 5 μg of pEFM2 obtained in Example 1 was dissolved in 50 μl of Y-100 buffer solution and 10 units of restriction enzyme XhoI and 8 units of HpaI were added. Digestion reaction was carried out at 37° C. for 3 hours. About 1 μg of a DNA fragment of about 2,700 bp containing the second half of env gene was obtained from the reaction solution by the LGT method.

0.05 pmole of the XhoI-StuI fragment (about 630 bp) derived from pAFG10 and 0.01 pmole of the XhoI-HpaI fragment (about 2,700 bp) derived from pEFM1 were dissolved in 40 μl of T4DNA ligase buffer. 5 units of T4DNA ligase was added and ligation reaction was carried out at 4° C. for 18 hours.

Figure 4:
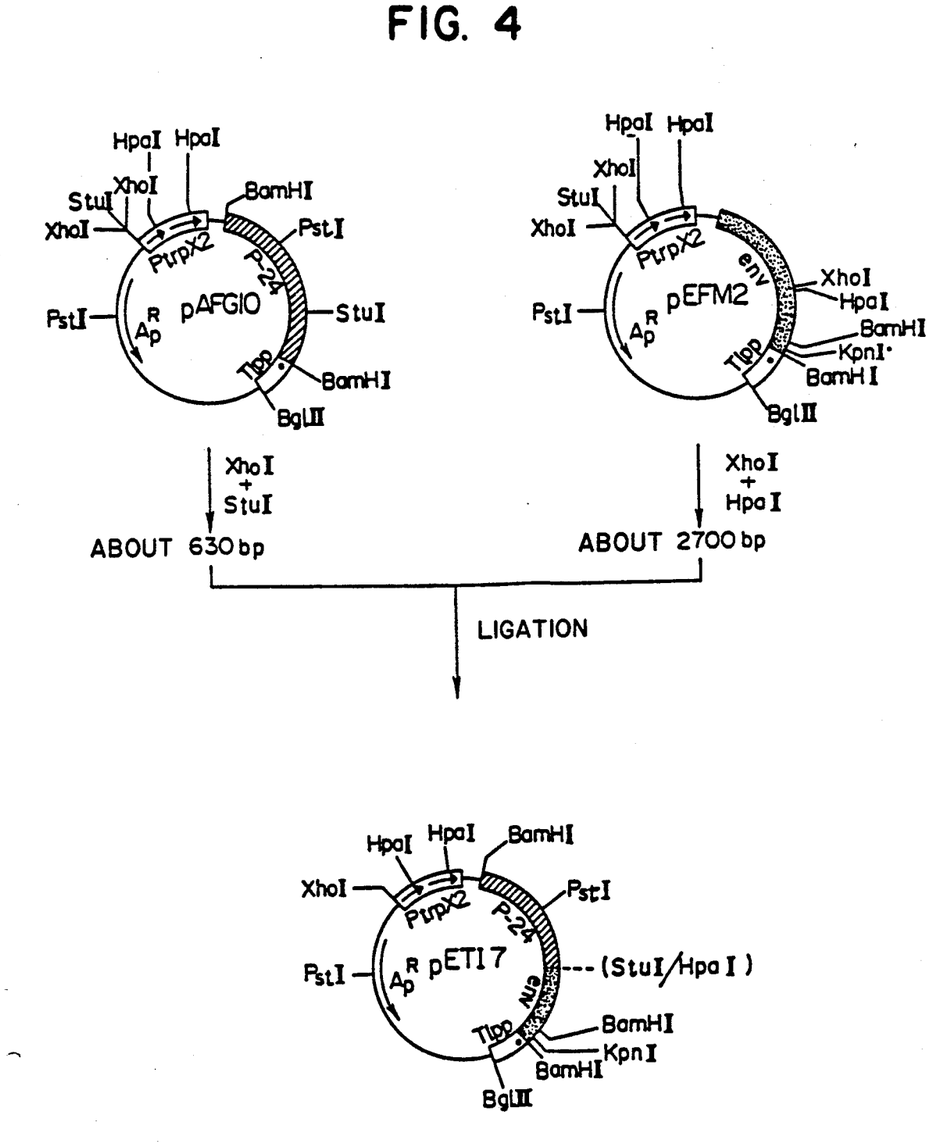
FIG. 4 shows the process for constructing plasmid pETI7.

*Escherichia coli* HB101 was transformed using the reaction solution to obtain Ap^R colonies. Plasmid DNA, pETI7 illustrated in FIG. 4 was recovered from one of the colonies by the method of Birnboim et al. The amino acid sequence of the fused polypeptide encoded by pETIb 7, wherein an antigen polypeptide encoded by gag gene and an antigen polypeptide encoded by env gene are fused, and the base sequence of the gene are shown in Table 3.

TABLE 3

```
                                          ─────────> amino acids encoded by p24 gene
          10        20        30        40        50        60
ATGGATCCATGGCAAATGAAAGACCTACAGGCCATTAAGCAAGAAGTCTCCCAAGCAGCC
Met Asp Pro Trp Gln Met Lys Asp Leu Gln Ala Ile Lys Gln Glu Val Ser Gln Ala Ala 70        80        90        100       110       120
CCTGGGAGCCCCCAGTTTATGCAGACCATCCGGCTTGCGGTGCAGCAGTTTGACCCCACT
Pro Gly Ser Pro Gln Phe Met Gln Thr Ile Arg Leu Ala Val Gln Gln Phe Asp Pro Thr 130       140       150       160       170       180
GCCAAAGACCTCCAAGACCTCCTGCAGTACCTTTGCTCCTCCCTCGTGGCTTCCCTCCAT
Ala Lys Asp Leu Gln Asp Leu Leu Gln Tyr Leu Cys Ser Ser Leu Val Ala Ser Leu His 190       200       210       220       230       240
CACCAGCAGCTAGATAGCCTTATATCAGAGGCCGAAACCCGAGGTATTACAGGTTATAAC
His Gln Gln Leu Asp Ser Leu Ile Ser Glu Ala Glu Thr Arg Gly Ile Thr Gly Tyr Asn 250       260       270       280       290       300
CCATTAGCCGGTCCCCTCCGTGTCCAAGCCAACAATCCACAACAACAAGGATTAAGGCGA
Pro Leu Ala Gly Pro Leu Arg Val Gln Ala Asn Asn Pro Gln Gln Gln Gly Leu Arg Arg 310       320       330       340       350       360
GAATACCAGCAACTCTGGCTCGCCGCCTTCGCCGCCCTGCCGGGGAGTGCCAAAGACCCT
Glu Tyr Gln Gln Leu Trp Leu Ala Ala Phe Ala Ala Leu Pro Gly Ser Ala Lys Asp Pro amino acids
encoded by p24 gene <────────────────────> amino acids encoded by env gene
          370       380       390       400       410       420
TCCTGGGCCTCTATCCTCCAAGGAACCCTACAAAGCACTAATTATACTTGCATTGTCTGT
Ser Trp Ala Ser Ile Leu Gln Gly Thr Leu Gln Ser Thr Asn Tyr Thr Cys Ile Val Cys 430       440       450       460       470       480
ATCGATCGTGCCAGCCTCTCCACTTGGCACGTCCTATACTCTCCCAACGTCTCTGTTCCA
Ile Asp Arg Ala Ser Leu Ser Thr Trp His Val Leu Tyr Ser Pro Asn Val Ser Val Pro 490       500       510       520       530       540
TCCTCTTCTTCTACCCCCCTCCTTTACCCATCGTTAGCGCTTCCAGCCCCCCACCTGACG
Ser Ser Ser Ser Thr Pro Leu Leu Tyr Pro Ser Leu Ala Leu Pro Ala Pro His Leu Thr 550       560       570       580       590       600
TTACCATTTAACTGGACCCACTGCTTTGACCCCCAGATTCAAGCTATAGTCTCCTCCCCC
Leu Pro Phe Asn Trp Thr His Cys Phe Asp Pro Gln Ile Gln Ala Ile Val Ser Ser Pro 610       620       630       640       650       660
TGTCATAACTCCCTCATCCTGCCCCCCTTTTCCTTGTCACCTGTTCCCACCCTAGGATCC
Cys His Asn Ser Leu Ile Leu Pro Pro Phe Ser Leu Ser Pro Val Pro Thr Leu Gly Ser amino acids encoded <────────────┐
by env gene
          670       680        │
CGCTCCCGCCGAGCGGTACCTAAG
Arg Ser Arg Arg Ala Val Pro Lys
```

EXAMPLE 4

Production in *Escherichia coli* Carrying pETI7 of the Fused Polypeptide Wherein an Antigen Polypeptide Encoded by gag Gene and an Antigen Polypeptide Encoded by env Gene are Fused

*Escherichia coli* W3110StrA (FERM BP-732) was transformed using recombinant plasmid pETI7 obtained in Example 3 by a conventional method. An $Ap^R$ colony was selected and inoculated into 8 ml of MCG medium [0.6% $Na_2HPO_4$, 0.3% $KH_2PO_4$, 0.5% NaCl, 0.1% $NH_4Cl$, 0.5% glucose, 0.5% casamino acid, 1 mM $MgSO_4$, 4 μg/ml vitamine $B_1$, pH 7.2]. Culturing was carried out at 30° C. for 18 hours. The culture broth was centrifuged at 8,000 rpm for 10 minutes to recover cells. The cells were suspended in Sample buffer of Laemmli. The suspension was subjected to SDS-polyacrylamide gel electrophoresis and staining with Coomassie Brilliant Blue to detect a polypeptide band of a molecular weight of about 25,000. The band was not detected in the case of *Escherichia coli* which does not carry the plasmid.

The molecular weight of the polypeptide coincided with the molecular weight of the hybrid antigen polypeptide (25,051.02) calculated from the structure of plasmid pETI7. The hybrid antigen polypeptide produced as above and p24 which is a gag gene product and produced by the method described in Japanese Patent Application No 24187/84 were examined on the reactivity with the serum of ATL patients. As the result, it was confirmed that the hybrid antigen polypeptide reacted with the sera of ATL patients which reacted with p24 as well as those which did not react with p24.

From the result, it was revealed that the hybrid antigen polypeptide was in the form wherein the antigen polypeptide encoded by gag gene of ATLV and the antigen polypeptide encoded by env gene of ATLV were fused. Therefore, it is considered that the hybrid antigen polypeptide is extremely effective for serum diagnosis to detect anti-ATLA antibodies.

What is claimed is:

1. A process for producing a hybrid antigen polypeptide having the amino acid sequence:

MetAspProTrpGlnMetLysAspLeuGlnAlaIleLysGlnGluValSerGlnAlaAla ProGlySerProGlnPheMetGlnThrIleArgLeuAlaValGlnGlnPheAspProThr AlaLysAspLeuGlnAspLeuLeuGlnTyrLeuCysSerSerLeuValAlaSerLeuHis HisGlnGlnLeuAspSerLeuIleSerGluAlaGluThrArgGlyIleThrGlyTyrAsn ProLeuAlaGlyProLeuArgValGlnAlaAsnAsnProGlnGlnGlnGlyLeuArgArg GluTyrGlnGlnLeuTrpLeuAlaAlaPheAlaAlaLeuProGlySerAlaLysAspPro SerTrpAlaSerIleLeuGlnGlyThrLeuGlnSerThrAsnTyrThrCysIleValCys IleAspArgAlaSerLeuSerThrTrpHisValLeuTyrSerProAsnValSerValPro SerSerSerSerThrProLeuLeuTyrProSerLeuAlaLeuProAlaProHisLeuThr LeuProPheAsnTrpThrHisCysPheAspProGlnIleGlnAlaIleValSerSerPro CysHisAsnSerLeuIleLeuProProPheSerLeuSerProValProThrLeuGlySer ArgSerArgArgAlaValProLys, which comprises culturing a microorganism carrying a replicable recombinant plasmid having an operative DNA fragment coding for said polypeptide in a culture medium until recoverable amounts of said polypeptide are produced and thereafter recovering said polypeptide therefrom.

2. The process according to claim 1, wherein the recombinant plasmid contains a tryptophan promoter.

3. The process according to claim 2, wherein the recombinant plasmid is pETI7.

4. The process according to claim 1, wherein the microorganism belongs to *Escherichia coli*.

* * * * *